United States Patent [19]

Kosary et al.

[11] 4,244,871
[45] Jan. 13, 1981

[54] SULFONAMIDO-BENZOIC ACID DERIVATIVES

[75] Inventors: Judit Kosáry; Endre Kasztreiner; Zsuzsa Huszti; Ágnes Kenessey; György Cseh; Veronika Szilágyi née Pap; Judit Stverteczky née Sztrókay, all of Budapest, Hungary

[73] Assignee: Richter Gedeon Vegyeszeti Gyar RT, Budapest, Hungary

[21] Appl. No.: 58,363

[22] Filed: Jul. 12, 1979

Related U.S. Application Data

[63] Continuation of Ser. No. 778,569, Mar. 17, 1977, abandoned.

[30] Foreign Application Priority Data

Mar. 18, 1976 [HU] Hungary .............................. GO 1334

[51] Int. Cl.$^3$ ................. C07C 103/22; C07C 143/80; C07D 265/28
[52] U.S. Cl. .............................. 260/239.7; 260/239.6; 260/239.8; 260/397.7 R; 424/228; 560/12
[58] Field of Search ............... 260/239.6, 239.7, 239.8, 260/397.7R; 424/228

[56] References Cited

U.S. PATENT DOCUMENTS

| 2,910,488 | 10/1959 | Novello | 260/397.7 R |
| 3,318,882 | 5/1967 | Schmidt | 544/459 |
| 3,346,568 | 10/1967 | Schmidt | 260/239.8 |
| 3,522,274 | 7/1970 | Santilli | 260/333 |
| 3,839,321 | 10/1974 | Weinstock | 260/239.6 |
| 3,843,662 | 10/1974 | Holland | 260/397.7 R X |
| 3,926,961 | 12/1974 | Ferrini | 260/239.7 |
| 3,933,802 | 1/1976 | Ferrini | 260/239.7 |

FOREIGN PATENT DOCUMENTS 2232457 1/1974 Fed. Rep. of Germany .... 260/397.7 R

OTHER PUBLICATIONS

Taylor et al., Biochemistry vol. 9, pp. 2638 to 2645 (1970).
Hamor et al., J. Pharm. Sci. vol. 52, pp. 102–103 (1963).
Siedel et al., Chem. Ber. vol. 99, pp. 345 to 352 (1966).
Hawking et al., The Sulphonamides, pp. 54 to 57, H. K. Lewis & Co. Ltd.
Goodman et al., The Pharmacological Basis of Therapeutics, 5th Ed. pp. 218–219, 1520 to 1523, MacMillan Co. NY (1976).
Arrigoni et al., Drugs of Today vol. 12, pp. 313–318 (1976).
Arrigoni et al., Drugs of the Future, pp. 118–122 (1976).
S. S. Chatterjee, Drugs of the Future 1, pp. 145–147 (1976).

Primary Examiner—John D. Randolph
Attorney, Agent, or Firm—Young & Thompson

[57] ABSTRACT

The invention relates to novel sulfonamidobenzoic acid derivatives having the general formula

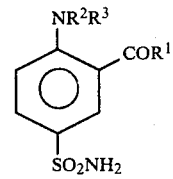

wherein
$R^1$ denotes a $C_{1-4}$ alkoxy group or a hydrazino group or an $NR^4R^5$ group, wherein $R^4$ and $R^5$ denote each a hydrogen atom or an identical or different $C_{1-4}$ alkyl group; furthermore $R^4$ may denote an aralkyl or substituted aralkyl group provided that $R^5$ denotes a hydrogen atom; furthermore $NR^4R^5$ may denote a morpholine or piperazine ring;
$R^2$ and $R^3$ may denote each a hydrogen atom or an identical or different $C_{1-4}$ aliphatic group; furthermore $R^2$ may denote a cycloaliphatic, aralkyl, substituted aralkyl or amino group provided that $R^3$ denotes a hydrogen atom; furthermore $R^2$ and $R^3$ may denote together with the adjacent nitrogen atom a morpholino ring, an unsubstituted piperazine ring or a substituted piperazine ring,
and to their pharmaceutically acceptable acid addition salts. Furthermore, the invention relates to a process for preparing these compounds.

The novel sulfonamidobenzoic acid derivatives having the general formula I possess significant tyrosine-paralyzing activity and thus they retard the biosynthesis of noradrenaline.

6 Claims, No Drawings

SULFONAMIDO-BENZOIC ACID DERIVATIVES

This is a continuation of application Ser. No. 778,569, filed Mar. 17, 1977, now abandoned.

This invention relates to novel compounds of pharmaceutical activity. More particularly, the invention relates to novel sulfonamido-benzoic acid derivatives having the general formula I

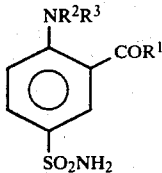

(I)

and the pharmaceutically acceptable acid addition salts thereof. Furthermore, the invention relates to a process for preparing these compounds.

In the formula:

$R^1$ denotes a $C_{1-4}$ alkoxy group or a hydrazino group or an $NR^4R^5$ group wherein $R^4$ and $R^5$ denote each a hydrogen atom or an identical or different $C_{1-4}$ alkyl group; furthermore $R^4$ may denote an aralkyl or substituted aralkyl group provided that $R^5$ denotes a hydrogen atom; furthermore $NR^4R^5$ may denote a morpholine or piperazine ring;

$R^2$ and $R^3$ may denote each a hydrogen atom or an identical or different $C_{1-4}$ aliphatic group; furthermore $R^2$ may denote a cycloaliphatic, aralkyl, substituted aralkyl or amino group provided that $R^3$ denotes a hydrogen atom; furthermore $R^2$ and $R^3$ may denote together with the adjacent nitrogen atom a morpholine ring, an unsubstituted piperazine ring or a substituted piperazine ring.

$R^1$ may denote e.g. a methoxy, amino, hydrazino, diethylamino, benzylamino, 4-chlorobenzylamino, or phenylpiperazino group.

$R^2$ and $R^3$ may denote together with the adjacent nitrogen atom e.g. a di-n-butylamino group, furthermore $R^2$ may denote e.g. an amino, cyclohexyl or 3,4-dimethoxyphenylethyl group provided that $R^3$ denotes a hydrogen atom, and $NR^2R^3$ may denote together e.g. an N-methylpiperazino group.

It is known that in the human organism and in the organism of higher developed animals noradrenaline is the principal substance which controls blood pressure (S. M. Rapaport: Medizinische Biochemie, VEB Verlag Volk and Gesundheit, Berlin, 1965, p. 720). The retardation of the biosynthesis of noradrenaline may lead to the decrease of abnormally high tension (O. Schier and A. Marxer: Arzneimittelforschung, Band 13, Birkäuser Verlag, Basel, 1969, p. 107). The first step in this biosynthesis is the hydroxylation of tyrosine, in which step the enzyme tyrosine-hydroxylase acts as biocatalyst.

Now it has been found that the novel sulfonamidobenzoic acid derivatives of the general formula I possess, in a quite surprising way, a significant paralysing effect on tyrosine-hydroxylase, and thus they are capable of retarding the biosynthesis of noradrenaline.

This recognition is surprising because, on the one hand, in the case of 2-amino-5-sulfonamidobenzoic acid known in literature (Chem. Berichte 99, 345/1966/) no tyrosine-hydroxylase paralyzing effect has been reported, and, on the other hand, among the tyrosine-hydroxylase paralyzing substances known in literature no sulfonamidobenzoic acid derivatives and not even their close analogues or related compounds are mentioned.

According to the invention the compounds of the general formula I can be prepared (a) by reacting a compound of the general formula II

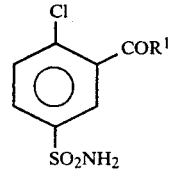

(II)

wherein $R^1$ has the same meaning as above, with an amine of the general formula $HNR^2R^3$, wherein $R^2$ and $R^3$ have the same meaning as above, and if desired, reacting the compound of the general formula I obtained in this way, provided that $R^1$ denotes a $C_{1-4}$ alkoxy group, with an amine of the general formula $HNR^4R^5$, wherein $R^4$ and $R^5$ have the same meaning as above, or with hydrazine, or (b) by reacting an acid of the general formula III

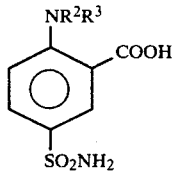

(III)

wherein $R^2$ and $R^3$ have the same meaning as above, or a reactive derivative thereof with a $C_{1-4}$ aliphatic alcohol or an amine of the general formula $HNR^4R^5$, wherein $R^4$ and $R^5$ have the same meaning as above, or with hydrazine and converting, if desired, the obtained free base with a pharmaceutically acceptable acid into an acid addition salt.

The conversion of the compounds of the general formula II into compounds of the general formula I is carried out expediently by allowing the compound of the general formula II to react with an excess of the amine of the general formula $HNR^2R^3$, using excess amine as solvent, preferably at a temperature of 100° to 170° C.

Of the compounds of the general formula II, the methyl and ethyl esters of 2-chloro-5-sulfonamidobenzoic acid are known from the literature (J. Pharm. Pharmacol. 14, 679/1962/).

Of the compounds of the general formula II thus far not described in literature, the carboxylic acid esters are prepared preferably by reacting 2-chloro-5-sulfonamidobenzoic acid known from literature (J. Pharm. Pharmacol. 14, 679/1962/) in a way known per se with a $C_{1-4}$ aliphatic alcohol. It is also possible to proceed so as to convert 2-chloro-5-sulfonamidobenzoic acid into a reactive derivative, e.g. into an acid chloride, preferably by means of thionyl chloride, and allow the product to react with an aliphatic alcohol. It is expedient to apply in this latter reaction an excess of the alcohol as solvent, and to maintain the temperature range between 0° C. and the boiling point of the solvent.

Of the compounds of the general formula II thus far not described in the literature, the acid amides can be prepared preferably by reacting 2-chloro-5-sulfonamidobenzoyl chloride with an amine of the general formula $HNR^4R^5$, wherein $R^4$ and $R^5$ have the same meaning as above. It is expedient to apply in this reaction water or an inert solvent, such as dichloroethane, chloroform or benzene, furthermore a basic acid-binding agent, such as triethylamine, or an alkali hydroxide, or to use the amine in an excess. The reaction can be carried out at a temperature ranging from 0° C. to the boiling point of the solvent.

The acid amides of the general formula II can be preferably prepared also by reacting the methyl or ethyl ester of 2-chloro-5-sulfonamidobenzoic acid with an amine of the general formula $HNR^4R^5$, wherein $R^4$ and $R^5$ have the same meaning as above. In this reaction methanol, ethanol or ethylene glycol as used as solvents.

The hydrazides of general formula II can be preferably prepared by reacting the methyl or ethyl ester of 2-chloro-5-sulfonamidobenzoic acid in a methanolic or ethanolic solution with hydrazine hydrate.

The conversion of acids of the general formula III into compounds of the general formula I can be carried out expediently as follows.

If a carboxylic acid ester is to be prepared, that is $R^1$ denotes a $C_{1-4}$ alkoxy group in the compound of the general formula I, at first the acid chloride is prepared from an acid of the general formula III. Thionyl chloride is used here as an agent forming the acid chloride, an excess of thionyl chloride serving as a solvent, if desired, in the presence of a few drops of pyridine as catalyst. The acid chloride obtained in this way is then allowed to react with a $C_{1-4}$ aliphatic alcohol, an excess of the alcohol serving preferably as solvent, at a temperature ranging from 0° C. to the boiling point of the alcohol. On preparing methyl and ethyl esters it is also possible to heat an acid of the general formula III in a methanolic or ethanolic solution containing gaseous hydrochloric acid.

If an acid amide is to be prepared, i.e. $R^1$ denotes an $NR^4R^5$ group, wherein $R^4$ and $R^5$ have the same meaning as above, the acid chloride prepared from a compound of the general formula III according to the method described above is allowed to react with an amine of the general formula $HNR^4R^5$, wherein $R^4$ and $R^5$ have the same meaning as above. In this reaction it is expedient to use an inert solvent, e.g. dichloroethane or chloroform, further a basic acidbinding agent, e.g. triethyl amine or an excess of the applied amine; furthermore it is expedient to carry out the reaction in the temperature range between 0° C. and the boiling point of the solvent.

If an acid hydrazide is to be prepared, i.e. $R^1$ denotes a hydrazine group in the compound of the general formula I, it is expedient to react the methyl or ethyl ester prepared from an acid of the general formula III in the above-described way with hydrazine in a methanolic or ethanolic solution at the boiling point of the reaction mixture.

Of the acids of the general formula II, 2-amino-5-sulfonamidobenzoic acid is known from literaure (Chem. Berichte, 99, 345/1966/). Other acids of the general formula III thus far not described in literature can be prepared preferably by allowing 2-chloro-5-sulfonamidobenzoic acid to react with an amine of the general formula $HNR^2R^3$, wherein $R^2$ and $R^3$ have the same meaning as above, using preferably an excess of the amine as solvent, expediently at a temperature of 100° to 170° C.

The acid addition salts of the compounds of the general formula I can be prepared preferably by dissolving a base of the general formula I e.g. in methanol, ethanol, isopropanol or ether, and adding to the solution under cooling dropwise the solution of the desired inorganic acid in methanol, ethanol or ether, or the solution of the desired inorganic acid in methanol, ethanol or ether, or the solution of the desired organic acid in methanol, ethanol, isopropanol, ether or acetone. The precipitated salt is separated by filtration and then recrystallized.

Hydrochloric acid, hydrobromic acid, sulfuric acid or phosphoric acid can be preferably applied as inorganic acids whereas tartaric acid, maleic acid, fumaric acid, methanesulfonic acid, ethanesulfonic acid or 4-toluenesulfonic acid as organic acids.

The tyrosine-hydroxylase inhibiting effect in vitro of the novel compounds prepared by the process according to the invention was determined by the Nagatsu-Udenfriend method (Anal. Biochem. 9, 122/1964/) in a rat-adrenal homogenizate. The inhibiting effect of some compounds is given in Table I.

Table 1

| Name of compound | Concentration mole | Tyrosine-hydroxylase activity (nmole/g tissue) hour | Inhibition % |
|---|---|---|---|
| Control | — | 1582+110 | — |
| 2-Cyclohexylamino-5-sulfonamidobenzoic acid amide hydrochloride | $10^{-3}$ | 0 | 100 |
| | $10^{-4}$ | 285±12 | 82 |
| | $10^{-5}$ | 506±25 | 78 |
| 1-(2-/4-Morpholino/-5-sulfonamidobenzoyl)-4-phenylpiperazine hydrochloride | $10^{-3}$ | 63±9 | 96 |
| | $10^{-4}$ | 886±18 | 44 |
| 2-(3,4-Dimethoxyphenylethylamino)-5-sulfonamidobenzoic acid hydrazide hydrochloride | $10^{-3}$ | 64±8 | 96 |
| | $10^{-4}$ | 902±81 | 43 |
| 2-Cyclohexalamino-5-sulfonamidobenzoic acid methyl ester hydrochloride | $10^{-3}$ | 158±21 | 90 |
| | $10^{-4}$ | 916±75 | 42 |
| 2-(4-Morpholino)-5-sulfonamidobenzoic acid methyl ester hydrochloride | $10^{-3}$ | 237±10 | 85 |
| | $10^{-4}$ | 948±72 | 40 |
| 2-(3,4-Dimethoxyphenylethylamino)-5-sulfonamidobenzoic acid methyl ester hydrochloride | $10^{-3}$ | 316±15 | 80 |
| | $10^{-4}$ | 1074±170 | 32 |

Then the noradrenaline-level decreasing effect of the compounds was determined in vivo, in rat heart by the method of Anton and Sayre (J. Pharm. Exp. Ther. 138, 360/1962/). Results obtained with 2-cyclohexylamino-5-sulfonamidobenzoic acid amide hydrochloride are presented in Table II.

Table II

| Treatment | Dose i.p. mg/kg | Period of treatment | Noradrenaline level in the heart μg/g tissue | Noradrenaline level in % of the control |
|---|---|---|---|---|
| Control | — | — | 1.01±0.12 | 100 |
| 2-Cyclohexyl-amino-5-sulfonamido-benzoic acid hydrochloride | 100 | 10 days | 0.60±0.07 | 60 |

The invention is elucidated in detail by the following non-limiting Examples.

EXAMPLE 1

2-(4-Morpholino)-5-sulfonamidobenzoic acid methyl ester

Method (a)

The mixture of 10 g. (0.04 moles) of 2-chloro-5-sulfonamidobenzoic acid methyl ester and 17.4 g. (0.2 moles) of morpholine is heated for 10 hours at 140° C., then excess morpholine is distilled off in vacuo, the distillation residue mixed up with 100 ml. of water and shaken with 300 ml. of methyl ethyl ketone. The organic phase is evaporated and the residue recrystallized from methanol.

Yield: 9 g., (75%); m.p.: 285° C.

In order to prepare the hydrochloride, the base is dissolved in methanol, the solution acidified with a methanolic solution of hydrochloric acid, evaporated in vacuo, the residue stirred with anhydrous ether, the obtained precipitate filtered and dried. The hydrochloride obtained in this way melts at 280° C. under decomposition.

The compounds of the general formula I and their acid addition salts prepared by the above method are presented in Table III.

Table III

| Compound | M.p. °C. | M.p. of the hydrochloride °C. |
|---|---|---|
| 2-Cyclohexylamino-5-sulfonamidobenzoic acid methyl ester | 285 | 155 (decomposition) |
| 2-(3,4-Dimethoxyphenyl-ethyl-amino)-5-sulfonamidobenzoic acid methyl ester | 90 | 110 (decomposition) |
| 2-(4-Methylpiperazino)-5-sulfonamidobenzoic acid methyl ester | 304–305 | |

Method (b)

Step "A"

2-(4-Morpholino)-5-sulfonamidobenzoic acid

The mixture of 35.25 g. (0.15 moles) of 2-chloro-5-sulfonamidobenzoic acid and 90 g. (1.035 moles) of morpholine is heated for 5 hours at 140° C., then excess morpholine is distilled off in vacuo. The distillation residue is dissolved in 300 ml. of water and the solution neutralized with 45 ml. of acetic acid. The formed crystalline precipitate is filtered, washed with some water and dried.

Yield: 40.8 g. (95%); m.p. 278°–281° C.

Further acids of the general formula III prepared by this process are presented in Table IV.

Table IV

| Compound | M.p. (°C.) | Note |
|---|---|---|
| 2-Cyclohexylamino-5-sulfonamidobenzoic acid | 200–202 | |
| 2-Benzylamino-5-sulfonamidobenzoic acid | 238–242 | After the reaction the distillation residue is dissolved in an aqueous solution of potassium carbonate, filtered, and the pure product is obtained by acidifying the filtrate with hydrochloric acid. |

Step "B"

2-(4-Morpholino)-5-sulfonamidobenzoic acid methyl ester 7 ml. (0.09 moles) of thionyl chloride are dropwise added to 90 ml. of anhydrous methanol under anhydrous conditions at a temperature of 5° to 10° C. in 20 minutes, and the mixture is stirred for further ten minutes. Then 17.17 g. (0.06 moles) of 2-(4-morpholino)-5-sulfonamidobenzoic acid prepared in the above-described way are added to the solution in 15 minutes at a temperature of 8 to 10° C. The mixture is allowed to stand overnight at room temperature, then refluxed for an hour under stirring and evaporated to dryness in vacuo. The residue is stirred with 200 ml. of ice-cold 10% ammonium hydroxide solution and shaken with 5×50 ml. of chloroform. On combining the organic extracts, they are dried on anhydrous magnesium sulfate, then the drying agent filtered off, and the solution evaporated to dryness in vacuo. The evaporation residue is recrystallized from isopropanol. Yield: 12.0 g. (66.7%).

EXAMPLE 2

2-Cyclohexylamino-5-sulfonamidobenzoic acid amide

Step "A"

2-Chloro-5-sulfonamidobenzoic acid amide

Gaseous ammonia is allowed to bubble at 150° C. for 5 hours through a solution of 10 g. (0.04 moles) of 2-chloro-5-sulfonamidobenzoic acid methyl ester. Then the solution is evaporated to dryness in vacuo, the evaporation residue rubbed with 50 ml. of water, the precipitate filtered and dried. Yield: 5.35 g. (57%); m.p. after recrystallization from water: 178° C.

Step "B"

2-Cyclohexylamino-5-sulfonamidobenzoic acid amide

The mixture of 2.35 g. (0.01 moles) of 2-chloro-5-sulfonamidobenzoic acid amide and 4.9 g. (0.05 moles) of cyclohexyl amine is heated for 10 hours at 140° C., then excess amine is distilled off in vacuo, the distillation residue stirred with 100 ml. of water and shaken with 300 ml. of methyl ethyl ketone. The organic solution is evaporated to dryness, and the evaporation residue recrystallized from a 2:1 mixture of water and acetone.

Yield: 2.5 g. (85%); m.p. 229° C.

M.P. of the hydrochloride: 232° C.

Further compounds of the general formula I prepared by the above method and their acid addition salts prepared by method (a) of Example 1 are presented in Table V.

Table V

| Compound | M.p.(°C.) | M.p.(°C.) of the hydrochloride |
|---|---|---|
| 2-(3,4-Dimethoxyphenyl-ethylamino)-5-sulfonamido-benzoic acid amide | 179 | 198 |
| 2-Hydrazino-5-sulfonamido-benzoic acid amide | 283 | 299 |

EXAMPLE 3

2-Cyclohexylamino-5-sulfonamidobenzoic acid hydrazide

Step "A"

2-Chloro-5-sulfonamidobenzoic acid hydrazide

To the mixture of 10 ml of 72% hydrazine hydrate (0.144 moles) and 25 ml. of methanol, 5.8 g. (0.023 moles) of 2-chloro-5-sulfonamidobenzoic acid methyl ester is added at room temperature. The mixture is stirred the whole day at room temperature, then allowed to stand overnight. On adding 40 ml. of water to the mixture and stirring, methanol is distilled off in vacuo, the precipitate-containing residue is filtered, and the solid substance is dried. Yield: 4.0 g. (70%); m.p. after recrystallization from water: 186° C.

The hydrochloride melts at 173° C. under decomposition.

Step "B"

2-Cyclohexylamino-5-sulfonamidobenzoic acid hydrazide

The mixture of 5.0 g. (0.02 moles) of 2-chloro-5sulfonoamidobenzoic acid hydrazide obtained in the way described in Step "A" and 9.8 g. (0.1 moles) of cyclohexyl amine is heated for 10 hours at 140° C., then excess amine is distilled off in vacuo, the residue on distillation is rubbed with 100 ml. of water and shaken with 300 ml. of methyl ethyl ketone. The organic solution is evaporated in vacuo and the residue recrystallized from methanol. Yield: 4.17 g. (67%); m.p.: 125°–127° C.

The dihydrochloride of the base melts at 145°–150° C. under decomposition.

The above process was applied also for the preparation of the following compound of the general formula I:

2-(3,4-dimethoxyphenyl-ethylamino)-5-sulfonamidobenzoic acid hydrazide; m.p.: 143° C.; m.p. of its dihydrochloride: 210° C. under decomposition.

EXAMPLE 4

2-Benzylamino-5-sulfonamidobenzoic acid benzylamide

The mixture of 9.96 g. (0.04 moles) of 2-chloro-5-sulfonamidobenzoic acid methyl ester and 17 g. (0.16 moles) of benzyl amine is heated for 10 hours at 140° C., then excess benzyl amine is distilled off in vacuo and the distillation residue rubbed with aqueous methanol. The obtained precipitate is filtered and dried. Yield: 4.9 g. (32%); m.p.: after recrystallization from acetic acid: 214°–217° C.

EXAMPLE 5

N-(2-/4-Morpholino/5-sulfonamidobenzoyl)-morpholine

Step "A"

2-Chloro-5-sulfonamidobenzoyl chloride

The mixture of 4.71 g. (0.02 moles) of 2-chloro-5-sulfonamidobenzoic acid and 28 ml. of thionyl chloride is boiled for 2 hours, then allowed to stand overnight at 4° C. The formed crystalline precipitate is filtered under suction under anhydrous conditions, washed with benzene and dried.

Yield: 4.5 g. (88.5%); m.p.: 141°–143° C.

Step "B"

N-(2-Chloro-5-sulfonamidobenzoyl)-morpholine 12.7 g. (0.05 moles) of 2-chloro-5-sulfonamidobenzoyl chloride prepared in the above-described way are added at a temperature of 0° to 5° C. in about 30 minutes to the solution of 15 g. (0.173 moles) of morpholine and 150 ml. of water. The mixture is stirred for 2 hours under cooling with icy water, then the precipitate is filtered, washed with water and dried. Yield: 12.6 g. (83%); m.p. after recrystallization from water: 160°–163° C.

Step "C"

N-(2-/4-Morpholino/5-sulfonamidobenzoyl)-morpholine

The mixture of 3.04 g. (0.01 moles) of N-(2-chloro-5-sulfonamidobenzoyl)-morpholine and 4.35 g. (0.05 moles) of morpholine is heated for 10 hours at 140° C., then the excess of amine is distilled off in vacuo and the residue recrystallized from water. Yield: 3.07 g. (80%); m.p.: 228° C.

EXAMPLE 6

1-(2-/4-Morpholino/-5-sulfonamidobenzoyl)-4-phenylpiperazine

Step "A"

1-(2-Chloro-5-sulfonamidobenzoyl)-4-phenylpiperazine

The solution of 15 g. (0.06 moles) of 2-chloro-5-sulfonamidobenzoyl chloride in 180 ml. of acetone is dropwise added to a mixture of 21.4 g. (0.126 moles) of 95% phenyl piperazine and 120 ml. of acetone at a temperature of 0° to 5° C. in an hour. Then the mixture is stirred for an hour at room temperature and subsequently refluxed for an hour under anhydrous conditions. Phenyl piperazine hydrochloride which precipitates as white crystals is filtered off, the acetonic filtrate is evaporated to a small volume and kept overnight in a refrigerator. The precipitated crystals are filtered and dried. Yield: 13.75 g. (53%); m.p.: 164°–165° C.

Step "B"

1-(2-/4-Morpholino/-5-sulfonamidobenzoyl)-4-phenyl piperazine

The mixture of 3.8 g. (0.01 moles) of 1-(2-chloro-5-sulfonamidobenzoyl)-4-phenyl piperazine and 4.35 g. (0.05 moles) of morpholine is heated for 10 hours at 140° C. Excess morpholine is distilled off in vacuo, and the residue on distillation is recrystallized from water. Yield: 3.68 g. (86%); m.p.: 143° C.

The hydrochloride melts at 182° C.

EXAMPLE 7

Pills containing each 250 mg. of active substance suitable for oral administration of therapeutical purposes can be prepared according to the below-given formulation:

| | |
|---|---|
| 2-Cyclohexylamino-5-sulfonamidobenzoic acid amide hydrochloride | 0.2500 g. |
| Potato starch | 0.0600 g. |
| Lactose | 0.0560 g. |
| Polyvinyl pyrrolidone | 0.0120 g. |
| Magnesium stearate | 0.0080 g. |
| Talc | 0.0120 g. |
| Colloidal silica | 0.0020 g. |

-continued

Average weight: 0.4000 g.

EXAMPLE 8

2-Cyclohexylamino-5-sulfonamido-benzoic acid isopropyl ester

Step "A"

2-chloro-5-sulfonamido-benzoic acid isopropyl ester 2.5 ml. of concentrated sulfuric acid are added dropwise to a stirred solution of 6.4 g. (0.027 moles) of 2-chloro-5-sulfonamido-benzoic acid in 64 ml. of isopropanol at a temperature not exceeding 40° C., and then the mixture is refluxed for 8 hours. The resulting solution is concentrated in vacuo to a small volume, and a 10% aqueous sodium hydroxide solution is added dropwise to the stirred concentrate until the pH of the mixture raises to 7. A precipitate separates. The resulting mixture is cooled to 4° C., the white, crystalline substance is filtered off, washed with water, dried and recrystallized from isopropanol. 5.15 g. (70%) of the title compound are obtained; m.p. 135° C.

Step "B"

2-Cyclohexylamino-5-sulfonamido-benzoic acid isopropyl ester

The 2-chloro-5-sulfonamido-benzoic acid isopropyl ester obtained as described in Step "A" above is converted to the title compound as described in Step "B" of Example 3.3.72 g. (55%) of the title compound are obtained; m.p.: 103° C. The hydrochloride melts at 212° C.

EXAMPLE 9

2-(4-morpholino)-5-sulfonamido-benzoic acid ethyl ester 2 ml. of concentrated sulfuric acid are added dropwise to a mixture of 2.86 g. (0.01 moles) of 2-(4-morpholino)-5-sulfonamido-benzoic acid (prepared as described in Step "A" of Method b of Example 1) and 150 ml. of absolute ethanol at a temperature not exceeding 40° C., and then the reaction mixture is refluxed for 8 hours. After 3 hours of boiling a clear solution is obtained. One-half of the solvent is evaporated in vacuo, the concentrate is cooled to 4° C, and the resulting white, crystalline substance is separated. 3.8 g. (92%) of 2-(4-morpholino)-5-sulfonamido-benzoic acid ethyl ester hydrosulfate are obtained; m.p.: 200° C.

EXAMPLE 10

N-[2-(4-Morpholino)-5-sulfonamido-benzoyl]-3,4-dimethoxy-phenyl-ethylamine

Step "A"

N-(2-Chloro-5-sulfonamido-benzoyl)-3,4-dimethoxyphenyl-ethylamine

A solution of 3.62 g. (0.022 moles) of 3,4-dimethoxyphenyl-ethylamine in 1 ml. of dry dioxane is added dropwise to a stirred solution of 2.54 g. (0.01 moles) of 2-chloro-5-sulfonamido-benzoyl chloride (prepared according to Step "A" of Example 5) in 10 ml. of dry dioxane at a temperature not exceeding 10° C. The reaction mixture is stirred at room temperature for 10 hours and then allowed to stand overnight at the same temperature. Thereafter 50 ml. of water are added to the mixture and the mixture is stirred at room temperature for one hour. The resulting white, crystalline substance is separated and recyrstallized from methanol to obtain 3.9 g. (60%) of the title compound; m.p.: 167° C.

N-[2-(4-Morpholino)-5-sulfonamido-benzoyl]-3,4-di methoxy-phenyl-ethylamine

The N-(2-chloro-5-sulfonamido-benzoyl)-3,4-dimethoxyphenyl-ethyl-amine prepared as described in Step "A" above is converted into the title compound as described in Step "C" of Example 5. 4.2 g. (93.6%) of the title compound are obtained; m.p.: 190° C. The hydrochloride melts at 198° C.

EXAMPLE 11

N-[2-(4-Morpholino)-5-sulfonamido-benzoyl]-4-methoxy-benzylamine

Step "A"

2-(4-Morpholino)-5-sulfonamido-benzoyl chloride

A mixture of 2.86 g. (0.01 moles) of 2-(4-morpholino)-5-sulfonamido-benzoic acid (prepared according to Step "A" of method b of Example 1), 14 ml. of thionyl chloride and 0.25 ml. of dry pyridine is refluxed until the gas evolution ceases (1.5 hours). The solution is evaporated to dryness, and the residue is crystallized from 10 ml. of ethyl acetate. 3.05 g. (about 100%) of the title compound are obtained. The product decomposes at 270° C. When subjected to atmospheric moisture, the product easily decomposes.

Step "B"

N-[2-(4-Morpholino)-5-sulfonamido-benzoyl]-4-methoxy- benzylamine

The 2-(4-morpholino)-5-sulfonamido-benzoyl chloride prepared as described in Step "A" above is dissolved in 10 ml. of dry dioxane, and a solution of 3.01 g. (0.022 moles) of 4-methoxy-benzylamine in 1 ml. of dry dioxane is added dropwise, with stirring, to the above solution at a temperature not exceeding 10° C. The reaction mixture is stirred at room temperature for 10 hours and then allowed to stand overnight. Thereafter the mixture is diluted with 100 ml. of water and the aqueous mixture is extracted with 5×50 ml. of methyl-ethyl-ketone. The methyl-ethyl-ketone phases are combined, washed with 4×50 ml. of distilled water in order to remove the water soluble hydrochloride of 4-methoxy-benzylamine, dried over sodium sulfate, filtered, and evaporated to dryness in vacuo. The residue is crystallized from a mixture of methanol and water. 1.6 g. (40%) of the title compound are obtained; m.p.: 152° C. The hydrochloride melts at 200° C.

2-(4-Morpholino)-5-sulfonamido-benzoic acid diethylamide, a further compound falling within the definition of formula (I), can be prepared in a similar manner. The free base melts at 272° C. whereas the hydrochloride melts at 358° C. under decomposition.

What we claim is:

1. 2-(4-Morpholino)-5-sulfonamidobenzoic acid methyl ester.
2. 2-Cyclohexylamino-5-sulfonamidobenzoic acid amide.
3. 2-Cyclohexylamino-5-sulfonamidobenzoic acid hydrazide.
4. 2-Benzylamino-5-sulfonamidobenzoic acid benzyl amide.
5. N-(2-/4-Morpholino/-5-sulfonamidobenzoyl)-morpholine.
6. 1-(2-/4-Morpholino/-5-sulfonamidobenzoyl)-4-phenylpiperazine.

* * * * *